(12) United States Patent
Ma et al.

(10) Patent No.: US 10,591,418 B2
(45) Date of Patent: Mar. 17, 2020

(54) FIBER-OPTIC MICRO-PROBES FOR MEASURING ACIDITY LEVEL, TEMPERATURE, AND ANTIGENS

(71) Applicants: The Curators of the University of Missouri, Columbia, MO (US); Clemson University, Clemson, SC (US)

(72) Inventors: Yinfa Ma, Rolla, MO (US); Honglan Shi, Rolla, MO (US); Qingbo Yang, Rolla, MO (US); Hai Xiao, Clemson, SC (US)

(73) Assignees: The Curators of the University of Missouri, Columbia, MO (US); Clemson University, Clemson, SC (US)

( * ) Notice: Subject to any disclaimer, the term of this patent is extended or adjusted under 35 U.S.C. 154(b) by 277 days.

(21) Appl. No.: 15/837,597

(22) Filed: Dec. 11, 2017

(65) Prior Publication Data

US 2018/0100806 A1 Apr. 12, 2018

Related U.S. Application Data

(63) Continuation-in-part of application No. 14/555,151, filed on Nov. 26, 2014, now abandoned.

(51) Int. Cl.
*G01N 21/77* (2006.01)
*G01N 21/64* (2006.01)
(Continued)

(52) U.S. Cl.
CPC ....... *G01N 21/7703* (2013.01); *G01N 21/645* (2013.01); *G01N 21/6428* (2013.01);
(Continued)

(58) Field of Classification Search
None
See application file for complete search history.

(56) References Cited

U.S. PATENT DOCUMENTS 5,098,659 A 3/1992 Yim et al.
5,337,376 A 8/1994 Ravetti et al.
(Continued)

OTHER PUBLICATIONS

International Search Report and Written Opinion dated Feb. 12, 2016, in PCT/US2015/060139, filed Nov. 11, 2015.
Yang, Qingbo et al. "Reflection-mode micro-spherical fiber-optic probes for in vitro real-time and single-cell level pH sensing," Sensors and Actuators B 207, Nov. 1, 2014, pp. 571-580.
Yuan, Lei et al. "All-in-fiber optofluidic sensor fabricated by femtosecond laser assisted chemical etching," Optic Letters, vol. 39 No. 8, Apr. 15, 2014, pp. 2358-2361.
(Continued)

*Primary Examiner* — Neil N Turk
(74) *Attorney, Agent, or Firm* — Hovey Williams LLP (57) ABSTRACT

A pH micro-probe, a temperature micro-probe, and an immuno-based micro-probe each include a shaft for transmuting an input light signal and a tip for inserting into a cell or other substance for measuring pH, temperature, and/or antigens. The pH micro-probe and the temperature micro-probe each include a luminescent material positioned on the tip of the micro-probe. The light signal excites the luminescent material so that the luminescent material emits a luminescent light signal. The luminescent light signal has a property value dependent on the pH or temperature being measured and reflects back through the shaft for being measured by a light signal measuring device. The immuno-based micro-probe includes a reflective material that has an effective refractive index dependent on the number of antigen-antibody bonds present on the reflective material.

15 Claims, 7 Drawing Sheets

(51) Int. Cl.
*G01N 31/22* (2006.01)
*G01N 21/76* (2006.01)
*G01N 21/80* (2006.01)

(52) U.S. Cl.
CPC ............ *G01N 21/76* (2013.01); *G01N 21/80* (2013.01); *G01N 31/221* (2013.01); *G01N 2021/6434* (2013.01); *G01N 2021/772* (2013.01); *G01N 2021/7786* (2013.01); *G01N 2201/0636* (2013.01); *G01N 2201/08* (2013.01)

(56) References Cited

U.S. PATENT DOCUMENTS

| | | |
|---|---|---|
| 5,370,119 A | 12/1994 | Mordon et al. |
| 2001/0043772 A1 | 11/2001 | Sorin |
| 2002/0173922 A1 | 11/2002 | Potyrailo |
| 2004/0047535 A1 | 3/2004 | Ukrainczyk |
| 2005/0069243 A1 | 3/2005 | Ukrainczyk |
| 2005/0265658 A1 | 12/2005 | Fan et al. |
| 2006/0257094 A1 | 11/2006 | McEvoy et al. |
| 2006/0263257 A1 | 11/2006 | Beauchamp et al. |
| 2007/0109550 A1 | 5/2007 | Ja et al. |
| 2008/0089635 A1 | 4/2008 | Hecht et al. |
| 2008/0265147 A1 | 10/2008 | Fan et al. |
| 2011/0236988 A1 | 9/2011 | Reed et al. |
| 2012/0230641 A1 | 9/2012 | Donlagic |

OTHER PUBLICATIONS

Lan, Xinwei, et al. "Reflection based extraordinary optical transmission fiber optic probe for refractive index sensing," Sensors and Actuators B 193, Nov. 23, 2013, pp. 95-99.

Wang et al., "Optical microresonator based on hollow sphere with porous wall for chemical sensing," Optics Letters, vol. 37, No. 1, Jan. 1, 2012, pp. 94-96.

Wang, Hanzheng, "Novel Optical Microresonators for Sensing Applications," Jan. 1, 2014, Clemson University Dissertation, 112 pages, tigerprints.clemson.edu.

Wang et al., "Fiber pigtailed thin wall capillary coupler for excitation of microsphere WGM resonator," Optics Express, vol. 21, No. 13, Jul. 1, 2013, 15834-9.

Office Action dated Oct. 26, 2016, in corresponding U.S. Appl. No. 14/555,151, filed Nov. 26, 2014.

Office Action dated Jun. 21, 2016, in corresponding U.S. Appl. No. 14/555,151, filed Nov. 26, 2014.

Office Action dated May 18, 2017, in corresponding U.S. Appl. No. 14/555,151, filed Nov. 26, 2014.

Office Action dated Sep. 15, 2017, in corresponding U.S. Appl. No. 14/555,151, filed Nov. 26, 2014.

Office Action dated Dec. 21, 2015, in corresponding U.S. Appl. No. 14/555,151, filed Nov. 26, 2014.

The International Preliminary Report on Patentability dated May 30, 2017, in PCT/US2015/060139, filed Nov. 11, 2015.

FIBER-OPTIC MICRO-PROBES FOR MEASURING ACIDITY LEVEL, TEMPERATURE, AND ANTIGENS

RELATED APPLICATIONS

The present application is a continuation-in-part (CIP) of earlier-filed pending U.S. Non-Provisional patent application Ser. No. 14/555,151, titled "FIBER-OPTIC MICRO-PROBES FOR MEASURING ACIDITY LEVEL, TEMPERATURE, AND ANTIGENS", filed Nov. 26, 2014. The present application claims priority benefit of the earlier-filed non-provisional patent application. The earlier-filed application is hereby incorporated by reference in its entirety into the present application.

GOVERNMENT INTERESTS

The present invention was developed with support from the U.S. government under a contract with the National Institute of Health, Contract No. 5R21GM104696-03. Accordingly, the U.S. government has certain rights in the present invention.

BACKGROUND

Probes are often used for measuring acidity level (pH), temperature, and antigens of substances and test samples. Conventional probes typically are too large to make localized measurements, thus making pH, temperature, and antigen measurements in micro scale such as in a single cell, in a specific local spot, and micro-scale gradient change difficult. This particularly prevents intracellular measurements from being taken. Some conventional probes can make intracellular measurements but not without destroying the cell being probed.

SUMMARY

The present invention solves the above-described problems and provides a distinct advance in the art of pH, temperature, and immuno-based probes.

A pH micro-probe constructed in accordance with an embodiment of the present invention comprises a shaft, an ultra-thin mirror coating applied to at least part of the shaft, a tip, and a luminescent dye-doped coating and an ultra-thin mirror coating applied to the tip. The tip of the pH micro-probe may be inserted into a biological cell or similar substance whose pH is being measured. An input light signal is transmitted into the shaft and reflected off of the mirror coating so as to continue traveling into the tip. The input light signal reflects off of the mirror coating applied to the tip so as to excite the luminescent dye-doped coating. The luminescent dye-doped coating emits a pH dependent luminescent light signal. The luminescent light signal travels back through the shaft for being measured by a light signal measuring device.

A temperature micro-probe constructed in accordance with another embodiment of the present invention comprises a shaft and mirror coating similar to the pH micro-probe and a tip that includes a microcavity extending into the tip and a luminescent material positioned on or in the microcavity. The tip of the temperature micro-probe is inserted into a substance whose temperature is being measured. An input light signal is transmitted through the shaft so as to excite the luminescent material. The luminescent material emits a temperature dependent luminescent light signal. The luminescent light signal travels back through the shaft for being measured by a light signal measuring device.

An immuno-based micro-probe constructed in accordance with yet another embodiment of the present invention comprises a shaft and mirror coating similar to the pH micro-probe and temperature micro-probe, a tip, and a thin film coated on the tip. The thin film includes a number of nano holes extending therethrough. The tip of the immuno-based micro-probe is inserted into a sample being measured. A number of antibodies will then be immobilized on the thin film. Antigens in the sample will begin to bond to the antibodies. An input light signal is transmitted through the shaft so that some of the input light signal reflects off of the thin film and some of the input light signal passes through the nano holes. The amount of light reflecting off of the thin film is dependent on the number of antigens or ratio of antigen-antibody bonds to total number of antibodies.

A pH micro-probe constructed in accordance with another embodiment of the present invention comprises a shaft and a tip. The shaft includes a central fiber and a plurality of surrounding fibers. The shaft is connected to the tip at the shaft's distal end and is tapered from its proximal end to its distal end.

The central fiber is connected to the tip at the shaft's distal end (i.e., a distal end of the central fiber is connected to the tip) and allows an input light signal from an input light source to travel therethrough towards and into the tip. The central fiber includes a mirror coating surrounding the central fiber and configured to guide the input light signal through the central fiber. The mirror coating may be applied to a portion or all of an outer surface of the central fiber and may be a thin film at least partially formed of silver, aluminum, gold, or other reflective material. The central fiber may be an elongated transparent member formed of glass or other suitable transparent material.

The surrounding fibers are connected to the tip at the shaft's distal end (i.e., distal ends of the surrounding fibers are connected to the tip) and allow a luminescent light signal to travel into and through the surrounding fibers from the tip. Each surrounding fiber includes a mirror coating surrounding the surrounding fiber and configured to reflect a luminescent light signal traveling through the surrounding fibers so as to guide the luminescent light signal through the surrounding fibers. Each mirror coating may be applied to a portion or all of an outer surface of one of the surrounding fibers and may be a thin film at least partially formed of silver, aluminum, gold, or other reflective material. The surrounding fibers are twisted around the central fiber and may be elongated transparent members formed of glass or other suitable transparent material. In one embodiment, the surrounding fibers are adjacent to each other and may include six surrounding fibers.

The tip is configured to contact or be inserted into a cellular substance and has a luminescent dye doped coating and a mirror coating. The tip is connected to the central fiber and the surrounding fibers at the shaft's distal end and has a diameter of between 3 and 5 micrometers. In one embodiment, the tip widens from the distal end of the shaft and has a rounded shape. Importantly, the tip affords optical communication of the luminescent signal arising from the input light signal received from the central fiber to propagate back through the surrounding fibers.

The luminescent dye doped coating interacts with the light signal to generate a pH dependent or other characteristic dependent luminescent light signal. The luminescent dye-doped coating may be a thin film at least partially formed of 2',7'-bis-(2-carboxyethyl)-5-(and-6)-carboxyfluorescein (BCECF) or similar material, and may include an aerogel or similar material, organically modified silicate (ORMOSIL) or similar material, or any other suitable material. The luminescent dye-doped coating may be applied to a portion or all of an outer surface of the tip and may have a thickness on the nano scale or micro scale. The luminescent dye-doped coating may be approximately 100 nm to approximately 2 µm thick. The luminescent dye-doped coating may overlap the shaft's distal end.

The mirror coating at least partially reflects the luminescent light signal within the tip and may be a thin film at least partially formed of silver, aluminum, gold, or other reflective material applied over the luminescent dye doped coating. The mirror coating may overlap the shaft's distal end.

In use, the tip of the pH micro-probe may be inserted into a biological cell or similar substance whose pH is being measured. The micro-probe can be connected at the shaft's proximal end to a light source such as a light ray generator for generating an input light signal. The input light signal is transmitted through the central fiber towards the shaft's distal end into the tip and the luminescent light signal is reflected back into the surrounding fibers at the shaft's distal end and through the surrounding fibers towards the shaft's proximal end. The micro-probe can also be connected to a light signal measuring device near the shaft's proximal end for receiving the luminescent light signal from the surrounding fibers so that a property value can be measured for determining the pH or other characteristic of the cellular substance.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

The drawing figures do not limit the present invention to the specific embodiments disclosed and described herein.

The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
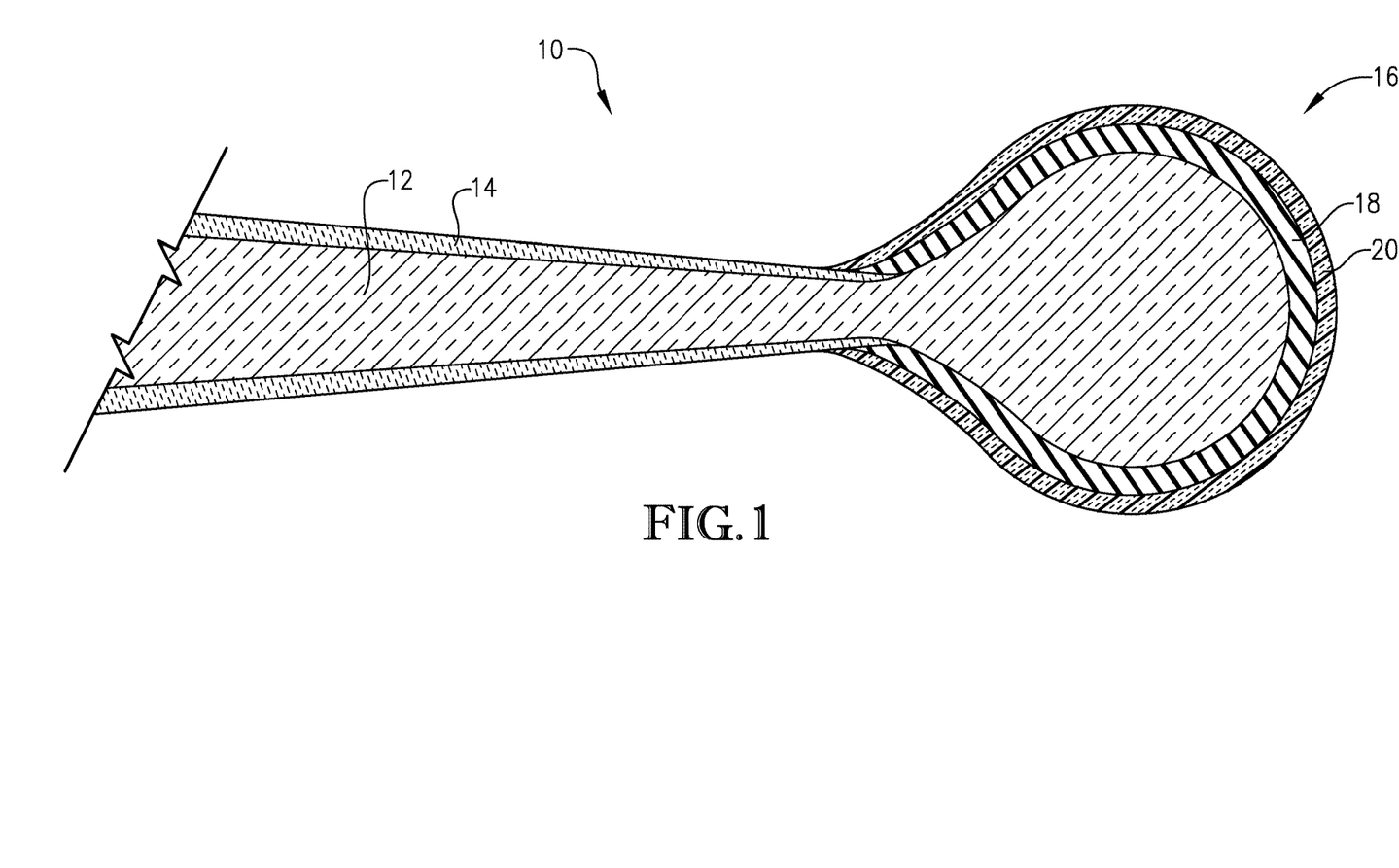
FIG. 1 is a partial vertical sectional view of a pH micro-probe constructed in accordance with an embodiment of the present invention.

Turning now to the drawing figures, and particularly FIG. 1, a pH micro-probe 10 constructed in accordance with an embodiment of the invention is illustrated. The micro-probe 10 broadly includes a shaft 12, a mirror coating 14 applied to at least part of the shaft 12, a tip 16, and a luminescent dye-doped coating 18 and a mirror coating 20 applied to at least part of the tip 16.

The shaft 12 allows a light signal to be transmitted therethrough and one embodiment of the shaft 12 is an elongated transparent member formed of glass or other suitable transparent material. The shaft 12 may be tapered so that a distal end of the shaft 12 is narrower or smaller than its proximal end. The shaft 12 also allows an output luminescent light signal to travel from the tip 16 and through the shaft 12, as described below.

The mirror coating 20 reflects the light signal traveling through the shaft 12 so as to guide the light signal through the shaft 12. The mirror coating 20 may be a thin film at least partially formed of silver, aluminum, gold, or other reflective material and may be applied to a portion or all of an outer surface of the shaft 12.

The tip 16 allows the luminescent dye-doped coating 18 to interact with the substance being tested and is positioned at the distal end of the shaft 12. The tip 16 may be the distal end of the shaft 12 itself or may be an extension or attachment connected to the shaft 12. The tip 16 may be bulb shaped (elongated, egg shaped, or spherical) and may be wider or larger than the distal end of the shaft 12.

The luminescent dye doped coating 18 interacts with the light signal to generate a pH dependent luminescent light signal. The luminescent dye-doped coating may be a thin film at least partially formed of 2',7'-bis-(2-carboxyethyl)-5-(and-6)-carboxyfluorescein (BCECF) or similar material, and may include an aerogel or similar material, organically modified silicate (ORMOSIL) or similar material, or any other suitable material. The luminescent dye-doped coating 18 may be applied to a portion or all of an outer surface of the tip 16 and may have a thickness on the nano scale or micro scale. In one embodiment the luminescent dye-doped coating 18 may be approximately 100 nm to approximately 2 μm thick.

The mirror coating 20 at least partially reflects the light signal within the tip 16 and may be a thin film at least partially formed of silver, aluminum, gold, or other reflective material applied over the luminescent dye doped coating 18.

Figure 2:
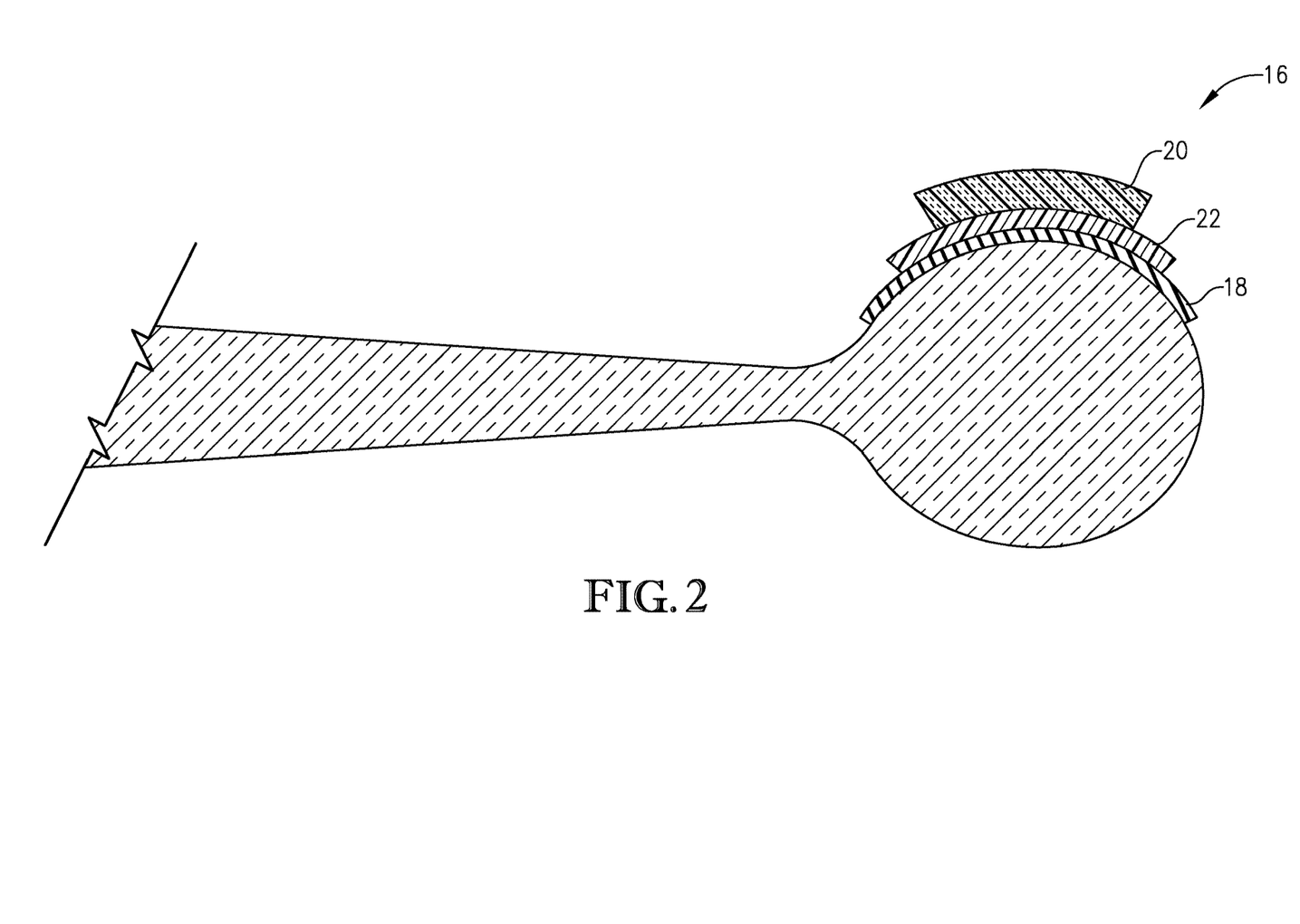
FIG. 2 is a partial vertical sectional view of a modified pH micro-probe.

In one embodiment, a protective film 22 such as a platinum belt may be applied between the luminescent dye doped coating 18 and the mirror coating 20, as shown in FIG. 2. The protective film 22 protects the luminescent dye doped coating 18 and the tip 16 from damage.

Use of the pH micro-probe 10 will now be described in more detail. The tip 16 of the pH micro-probe 10 may be inserted into a micro-volume solution or the intracellular or intercellular substance (cytoplasm, etc.) of a cell. An input light signal is then transmitted from a light signal generator into the proximal end of the shaft 12. The light signal will reflect off of the mirror coating 20 so as to continue traveling through the shaft 12 to the distal end of the shaft 12. The light signal will then continue into the tip 16 and will reflect off of the mirror coating 20 so as to bounce around inside the tip 16. The light signal will hit and be at least partially absorbed by the luminescent dye doped coating 18. The dye doped coating 18 will emit a luminescent light signal such as a fluorescent light signal. The luminescent light signal will reflect inside of the tip 16 and eventually exit the tip 16 into the shaft 12. The luminescent light signal will reflect off of the mirror coating 14 so as to continue traveling from the distal end of the shaft 12 to the proximal end of the shaft 12. The luminescent light signal will then exit the proximal end of the shaft 12 and continue traveling through fiber optic components to a light signal measuring device.

The luminescent light signal has a property value indicative of the pH of the measured substance. For example, the intensity of the luminescent light signal may be dependent on the pH of the substance. A fluorescence ratio (the ratio of the fluorescence of the luminescent dye doped coating 18 when excited at a first wavelength compared to a second wavelength (e.g. 560 nm compared to 640 nm) may also be measurable against the pH of the substance.

The above-described pH micro-probe 10 provides several advantages over conventional pH measuring methods. For example, the pH micro-probe 10 allows the pH of the cellular substance of a single cell or a very small sample to be measured. The pH micro-probe 10 confines the pH measurement to the cellular or other substance in contact with the tip 16 so that the pH of adjacent cells or adjacent material does not affect the measurement. This is particularly useful in heterogeneous environments such as biological cells. The pH micro-probe 10 also allows for the measurement of pH via fluorescence ratios, which eliminates the need to account for certain factors such as how much dye doped coating 20 is used.

Figure 3:
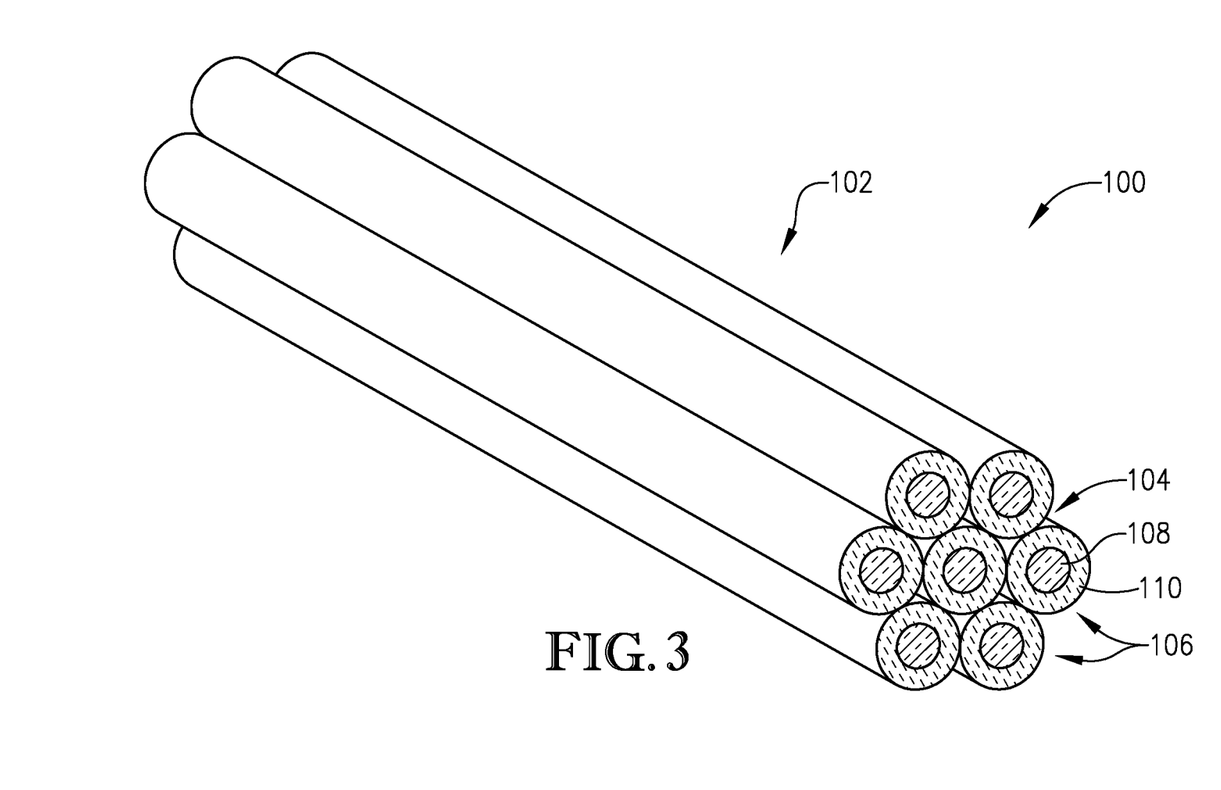
FIG. 3 is a perspective view of a pH micro-probe having a number of fiber optic fibers.

In another embodiment of the invention, a pH micro-probe 100 similar to the above-described micro-probe 10 includes a shaft 102 having a central fiber 104 and one or more surrounding fibers 106, as shown in FIG. 3.

The central fiber 104 allows an input light source to travel therethrough and includes a core 108 similar to the shaft 12 and a mirror coating 110 similar to the mirror coating 20 described above.

The surrounding fibers 106 allow the luminescent light signal to travel therethrough and each include a core and mirror coating similar to the core 108 and mirror coating 110 of the central fiber 104. The surrounding fibers 106 may be twisted around the central fiber 104 or may maintain an initial orientation in relation to the central fiber 104. In one embodiment there are six surrounding fibers 106 forming a hexagonal pattern around the central fiber 104.

The pH micro-probe 100 is used in substantially the same manner as the pH micro-probe 10 described above except that the light signal is transmitted through the central fiber 104 and the luminescent light signal is reflected back through the surrounding fibers 106 and optionally the central fiber 104.

Figure 4:
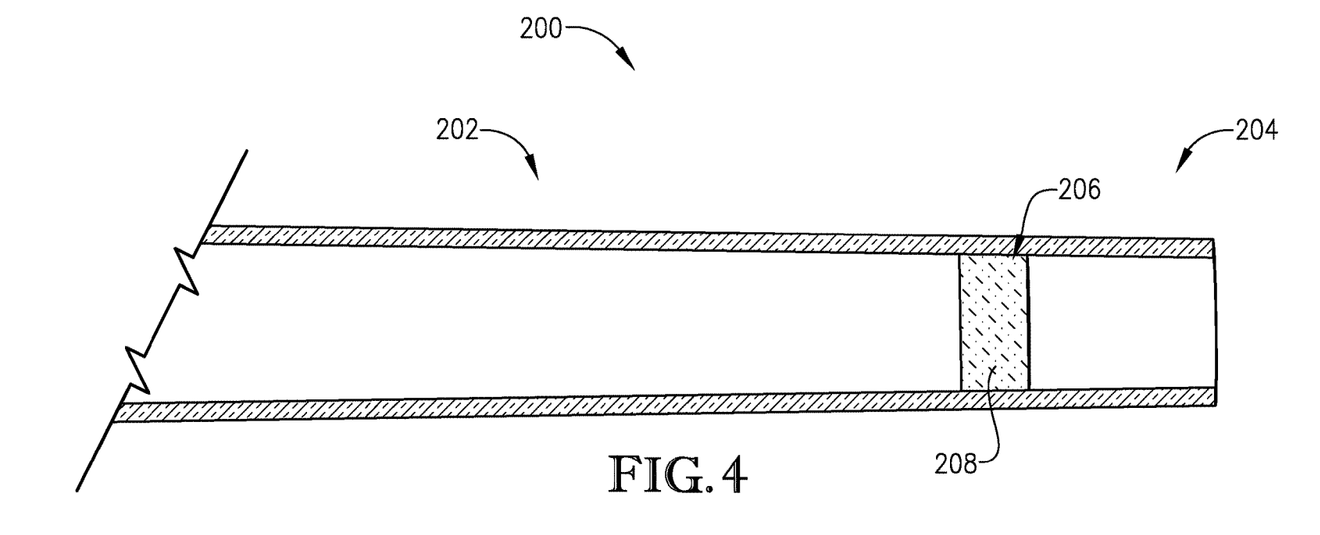
FIG. 4 is a partial vertical sectional view of a temperature micro-probe constructed in accordance with another embodiment of the present invention.

Turning now to FIG. 4, a temperature micro-probe 200 constructed in accordance with another embodiment of the invention is illustrated. The temperature micro-probe 200 broadly includes a shaft 202, a tip 204, at least one microcavity 206 extending into the tip 204, and a luminescent material 208 positioned in the microcavity 206.

The shaft 202 allows a light signal to be transmitted therethrough and may be substantially similar to the shaft 12 described above.

The tip 204 allows the light signal to interact with the luminescent material 208 and may be substantially similar to the tip 16 described above. In one embodiment, the tip 204 is the distal end of the shaft 202.

The microcavity 206 allows the luminescent material 208 to adhere to the tip 204 and interact with the light signal and may be formed in the tip 204 near the distal end of the shaft 202. The microcavity 206 may be formed by chemical etching via hydrofluoric acid (such as a 20% hydrofluoric acid solution) and may extend less than 30 μm along the tip 204. In one embodiment, the microcavity 206 has a volume of 5 μm by 5 μm by 5 μm or less.

The luminescent material 208 interacts with the light signal to generate a temperature dependent luminescent light signal and may be a thin film or coating of fluorescent material or a number of quantum dots. In one embodiment, the luminescent material 208 is a Rhodamine dye such as R6G. In another embodiment, the luminescent material 208 is a number of quantum dots in a liquid phase or solid phase coating on the surface. In yet another embodiment, the luminescent material 208 is a phosphor or phosphorescent material Use of the temperature micro-probe 200 will now be described n more detail. The tip 204 of the temperature micro-probe 200 is inserted into the substance whose temperature is to be measured. An input light signal is then transmitted into the proximal end of the shaft 202 from a light signal generator. The light signal travels to the distal end of the shaft 202 until it reaches the microcavity 206. The light signal will then be at least partially absorbed by the luminescent material 208. The luminescent material 208 will emit a luminescent light signal such as a fluorescent light signal. The luminescent light signal will travel to the proximal end of the shaft 202, exit the proximal end of the shaft 202, and continue traveling through fiber optic components to a light signal measuring device.

The luminescent light signal has a property value indicative of the temperature of the substance. For example, the wavelength of the luminescent light signal may be dependent on the temperature of the substance. In one embodiment, the full width of half of the maximum value of the wavelength (FWHM) may be measured. As another example, the intensity or peak intensity of the luminescent light signal at a specified wavelength may be dependent on the temperature of the substance. In another embodiment, the luminescent decay time may be measured to determine the temperature of the substance. As an example, the luminescent decay time of phosphor may be dependent on temperature.

The above-described temperature micro-probe 200 provides several advantages over conventional temperature measuring instruments. For example, the temperature micro-probe 200 allows the temperature of very small amounts of substances (including intracellular and intercellular substances) to be measured. The temperature micro-probe 200 allows for localized measurements to be made without influence of nearby temperatures. This is particularly useful in heterogeneous environments such as biological cells.

Figure 5:
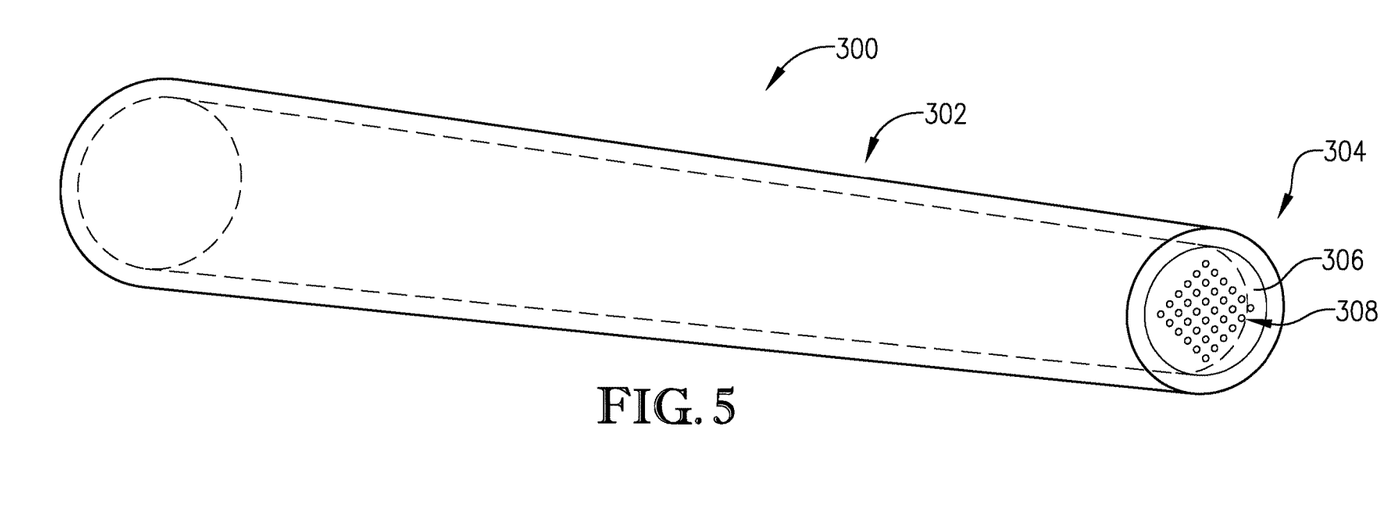
FIG. 5 is a partial perspective view of an immune-based micro-probe constructed in accordance with another embodiment of the present invention.
Figure 6:
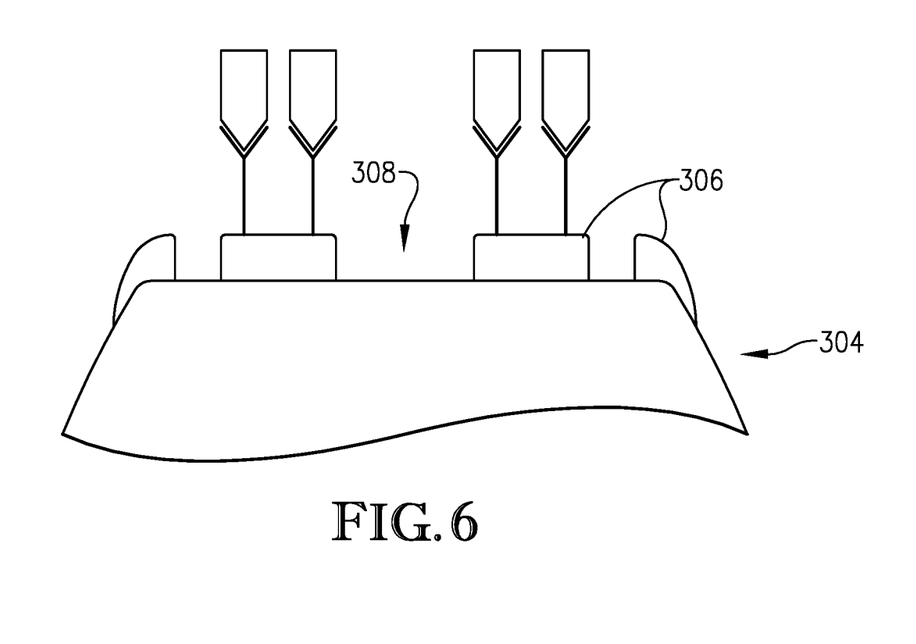
FIG. 6 is an enlarged partial vertical sectional view of a tip of the immuno-based micro-probe in FIG. 5.

Turning now to FIGS. 5 and 6, an immuno-based micro-probe 300 constructed in accordance with another embodiment of the invention is illustrated. The immuno-based micro-probe 300 broadly includes a shaft 302, a tip 304, a thin film 306, and a number of nano holes 308.

The shaft 302 allows a light signal to be transmitted therethrough and may be substantially similar to the shafts 12, 202 described above.

The tip 304 allows the light signal to interact with the thin film 306 and may be substantially similar to the tips 16, 204 described above. In one embodiment, the tip 304 is the distal end of the shaft 302.

The thin film 306 allows half antibodies to be immobilized thereon and may be applied to or coated on at least a portion of the tip 304. The thin film 306 may be formed of gold or any other suitable material.

The nano holes 308 allow at least a portion of the light signal to pass through the thin film 306 and extend through the thin film 306 so that the thin film 306 exhibits a porous texture.

Use of the immuno-based micro-probe 300 will now be described in more detail. The tip 304 of the immuno-based micro-probe 300 is inserted into a sample to be measured. An input light signal is then transmitted into the proximal end of the shaft 302 from a light signal generator. The light signal will travel to the distal end of the shaft 302 and will continue into the tip 304. Some of the input light signal will reflect off of the thin film 306 and some of the input light signal will pass through the nano holes 308 Antigens in the sample will bind to a layer of half antibodies immobilized on the thin film 306. As more antigens bind to the antibodies, the reflection intensity at spectral wavelength will increase. That is, more of the input light signal will reflect back into the shaft 302 for being detected by a light signal measuring device. As such, the number of antigen-antibody bonds or the ratio of antigen-antibody bonds to non-bonds can be measured as a function of the measured reflection intensity of the reflected light signal.

The above-described immuno-based micro-probe 300 provides several advantages over conventional immuno-based detection methods. For example, the immuno-based micro-probe 300 allows the antigens of a very small sample, such as a single cell, to be measured. The immuno-based micro-probe 300 allows for localized measurements to be made. This is particularly useful in heterogeneous environments.

Figure 7:
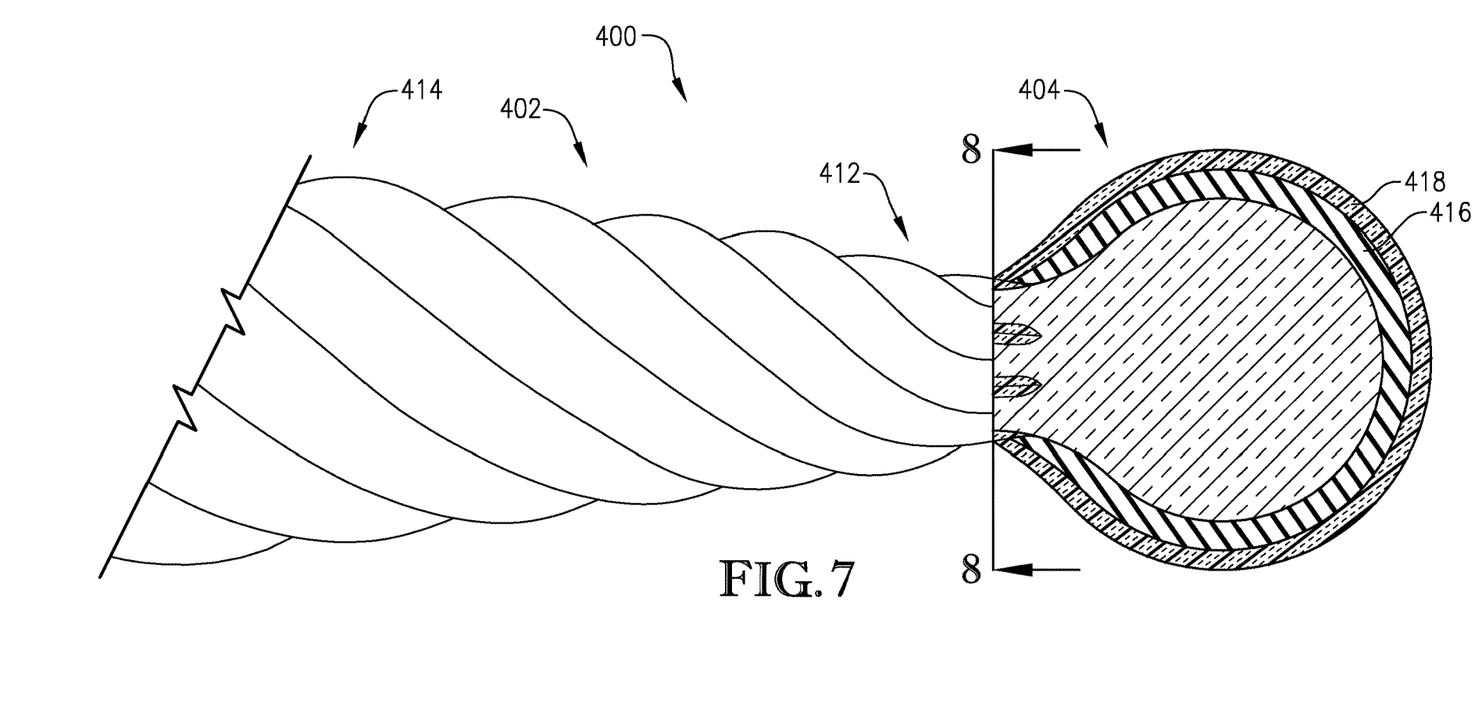
FIG. 7 is a partial cutaway elevation view of a pH micro-probe constructed in accordance with another embodiment of the present invention.
Figure 8:
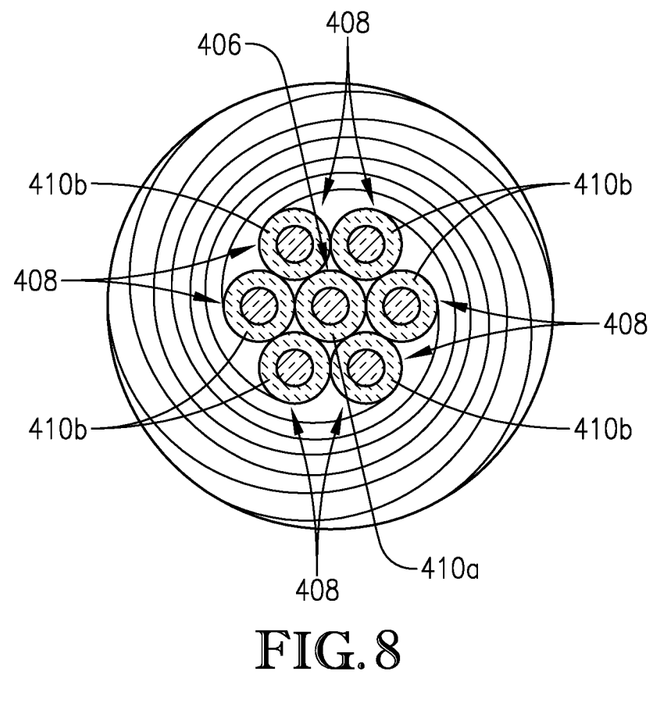
FIG. 8 is a cutaway elevation view of the pH micro-probe of FIG. 7.

Turning now to FIGS. 7 and 8, a pH micro-probe 400 constructed in accordance with another embodiment of the invention is illustrated. The micro-probe 400 broadly comprises a shaft 402 and a tip 404.

The shaft 402 includes a central fiber 406 and a plurality of surrounding fibers 408. The shaft 402 is connected to the tip 404 at the shaft's distal end 412 and is tapered from its proximal end 414 to its distal end 412.

The central fiber 406 is connected to the tip 404 at the shaft's distal end 412 (i.e., a distal end of the central fiber 406 is connected to the tip 404) and allows an input light signal from an input light source to travel therethrough towards and into the tip 404. The central fiber 406 includes a mirror coating 410a surrounding the central fiber 406 and configured to guide the input light signal through the central fiber 406. The mirror coating 410a may be applied to a portion or all of an outer surface of the central fiber 406 and may be a thin film at least partially formed of silver, aluminum, gold, or other reflective material. The central fiber 406 may be an elongated transparent member formed of glass or other suitable transparent material.

The surrounding fibers 408 are connected to the tip 404 at the shaft's distal end 412 (i.e., distal ends of the surrounding fibers 408 are connected to the tip 404) and allow a luminescent light signal to travel into and through the surrounding fibers 408 from the tip 404. Each surrounding fiber 408 includes a mirror coating 410b surrounding the surrounding fiber 408 and configured to reflect a luminescent light signal traveling through the surrounding fibers 408 so as to guide the luminescent light signal through the surrounding fibers 408. Each mirror coating 410b may be applied to a portion or all of an outer surface of one of the surrounding fibers 408 and may be a thin film at least partially formed of silver, aluminum, gold, or other reflective material. The surrounding fibers 408 are twisted around the central fiber 406, as best seen in FIG. 8, and may be elongated transparent members formed of glass or other suitable transparent material. In one embodiment, the surrounding fibers 408 are adjacent to each other and may include six surrounding fibers, as shown in FIG. 8.

The tip 404 is configured to contact or be inserted into a cellular substance and has a luminescent dye doped coating 416 and a mirror coating 418. The tip 404 is connected to the central fiber 406 and the surrounding fibers 408 at the shaft's distal end 412 and has a diameter of between 3 and 5 micrometers. In one embodiment, the tip 404 widens from the shaft's distal end 412 and has a rounded shape. Importantly, the tip 404 affords optical communication of the luminescent signal arising from the input light signal received from the central fiber 406 to propagate back through the surrounding fibers 408.

The luminescent dye doped coating 416 interacts with the light signal to generate a pH dependent or other characteristic dependent luminescent light signal. The luminescent dye-doped coating 416 may be a thin film at least partially formed of 2',7'-bis-(2-carboxyethyl)-5-(and-6)-carboxyfluorescein (BCECF) or similar material, and may include an aerogel or similar material, organically modified silicate (ORMOSIL) or similar material, or any other suitable material. The luminescent dye-doped coating 416 may be applied to a portion or all of an outer surface of the tip 404 and may have a thickness on the nano scale or micro scale. The luminescent dye-doped coating 416 may be approximately 100 nm to approximately 2 μm thick. The luminescent dye-doped coating 416 may overlap the shaft's distal end 412, as shown in FIG. 7.

The mirror coating 418 at least partially reflects the luminescent light signal within the tip 404 and may be a thin film at least partially formed of silver, aluminum, gold, or other reflective material applied over the luminescent dye doped coating 416. The mirror coating 418 may overlap the shaft's distal end 412, as shown in FIG. 7.

Use of the micro-probe 400 will now be described in detail. The tip 404 of the pH micro-probe 400 may be inserted into a biological cell or similar substance whose pH is being measured. The micro-probe 400 can be connected at the shafts proximal end 414 to a light source such as a light ray generator for generating an input light signal. The input light signal is transmitted through the central fiber 406 towards the shaft's distal end 412 into the tip 404 and the luminescent light signal is reflected back into the surrounding fibers 408 at the shaft's distal end 412 and through the surrounding fibers 408 towards the shafts proximal end 414. The micro-probe 400 can also be connected to a light signal measuring device near the shaft's proximal end 414 for receiving the luminescent light signal from the surrounding fibers 408 so that a property value can be measured for determining the pH or other characteristic of the cellular substance.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A micro-probe for measuring a non-cellular substance or an intracellular or intercellular pH of a cellular substance of a single cell, the micro-probe comprising:
    an elongated transparent shaft having opposing proximal and distal ends and tapering from the proximal end to the distal end such that the distal end is narrower than the proximal end, the shaft including a central fiber and a plurality of surrounding fibers twisted around the central fiber;
    a mirror coating applied to at least a part of the central fiber;
    mirror coatings applied to at least a part of the surrounding fibers;
    a tip extending from the central fiber and surrounding fibers at the distal end of the shaft for contacting or being inserted into the substance;
    a luminescent dye doped coating applied to at least part of the tip; and
    a mirror coating applied to at least part of the tip,
    wherein the micro-probe is configured such that:
        a light ray transmitted through the central fiber will reflect off of the mirror coating of the central fiber so as to continue travelling through the central fiber towards the distal end of the shaft, enter into the tip, reflect off of the mirror coating of the tip, and be at least partially absorbed by the luminescent dye doped coating so that the luminescent dye doped coating emits a luminescent light signal having a property value indicative of the pH of the cellular substance, and
        the luminescent light signal will pass from the tip into the surrounding fibers near the distal end of the shaft and reflect off of the mirror coatings of the surrounding fibers so as to propagate through the surrounding fibers towards the proximal end of the shaft so that the property value can be measured from the luminescent light signal for determining the pH of the cellular substance.

2. The micro-probe of claim 1, wherein the tip widens from the distal end of the shaft and has a rounded shape.

3. The micro-probe of claim 1, wherein the dye doped coating is formed of 2',7'-bis-2-carboxyethyl)-5-(and-6)-carboxyfluorescein (BCECF).

4. The micro-probe of claim 1, wherein the dye doped coating comprises an aerogel.

5. The micro-probe of claim 1, wherein the dye doped coating comprises an organically modified silicate.

6. The micro-probe of claim 1, wherein the surrounding fibers are adjacent to each other.

7. The micro-probe of claim 1, wherein the surrounding fibers include six surrounding fibers.

8. A micro-probe for measuring a non-cellular substance or an intracellular or intercellular pH of a cellular substance of a single cell, the micro-probe comprising:
    an elongated transparent shaft having opposing proximal and distal ends and tapering from the proximal end to the distal end such that the distal end is narrower than the proximal end, the shaft including a central fiber and a plurality of surrounding fibers twisted around the central fiber;
    a mirror coating applied to at least a part of the central fiber;
    mirror coatings applied to at least a part of the surrounding fibers;
    a tip extending from the central fiber and surrounding fibers at the distal end of the shaft for contacting or being inserted into the substance, the tip having a diameter of between 3 and 5 micrometers;
    a luminescent dye doped coating applied to at least part of the tip, the luminescent dye doped coating being between approximately 100 nanometers thick to approximately 2 micrometers thick; and
    a mirror coating applied to at least part of the tip,
    wherein the micro-probe is configured such that:
        a light ray transmitted through the central fiber will reflect off of the mirror coating of the central fiber so as to continue travelling through the central fiber towards the distal end of the shaft, enter into the tip, reflect off of the mirror coating of the tip, and be at least partially absorbed by the luminescent dye doped coating so that the luminescent dye doped coating emits a luminescent light signal having a property value indicative of the pH of the cellular substance, and
        the luminescent light signal will pass from the tip into the surrounding fibers near the distal end of the shaft and reflect off of the mirror coatings of the surrounding fibers so as to propagate through the surrounding fibers towards the proximal end of the shaft so that the property value can be measured from the luminescent light signal for determining the pH of the cellular substance.

9. The micro-probe of claim 8, wherein the tip widens from the distal end of the shaft and has a rounded shape.

10. The micro-probe of claim 8, wherein the dye doped coating is formed of 2',7'-bis-(2-carboxyethyl)-5-(and-6)-carboxyfluorescein (BCECF).

11. The micro-probe of claim 8, wherein the dye doped coating comprises an aerogel.

12. The micro-probe of claim 8, wherein the dye doped coating comprises an organically modified silicate.

13. The micro-probe of claim 8, wherein the surrounding fibers are adjacent to each other.

14. The micro-probe of claim 8, wherein the surrounding fibers include six surrounding fibers.

15. A micro-probe for measuring a non-cellular substance or an intracellular or intercellular pH of a cellular substance of a single cell, the micro-probe comprising:
- an elongated transparent shaft having opposing proximal and distal ends and tapering from the proximal end to the distal end such that the distal end is narrower than the proximal end, the shaft including a central fiber and six surrounding fibers adjacent to each other and twisted around the central fiber;
- a mirror coating applied to at least a part of the central fiber;
- mirror coatings applied to at least a part of the surrounding fibers;
- a tip extending from the central fiber and surrounding fibers at the distal end of the shaft for contacting or being inserted into the substance, the tip having a rounded shape with a diameter of between 3 and 5 micrometers;
- a luminescent dye doped coating applied to at least part of the tip, the luminescent dye doped coating comprising an aerogel and being between approximately 100 nanometers thick to approximately 2 micrometers thick; and
- a mirror coating applied to at least part of the tip, wherein the micro-probe is configured such that:
- a light ray transmitted through the central fiber will reflect off of the mirror coating of the central fiber so as to continue travelling through the central fiber towards the distal end of the shaft, enter into the tip, reflect off of the mirror coating of the tip, and be at least partially absorbed by the luminescent dye doped coating so that the luminescent dye doped coating emits a luminescent light signal having a property value indicative of the pH of the cellular substance, and
- the luminescent light signal will pass from the tip into the surrounding fibers near the distal end of the shaft and reflect off of the mirror coatings of the surrounding fibers so as to propagate through the surrounding fibers towards the proximal end of the shaft so that the property value can be measured from the luminescent light signal for determining the pH of the cellular substance.

* * * * *

UNITED STATES PATENT AND TRADEMARK OFFICE
CERTIFICATE OF CORRECTION

PATENT NO. : 10,591,418 B2
APPLICATION NO. : 15/837597
DATED : March 17, 2020
INVENTOR(S) : Ma et al.

Page 1 of 1

It is certified that error appears in the above-identified patent and that said Letters Patent is hereby corrected as shown below:

In the Specification

Replace the paragraph at Column 1, Lines 19-23 with the following text:
"This invention was made with government support under Contract No. 5R21GM104696-03 awarded by the National Institutes of Health. The government has certain rights in the invention."

Signed and Sealed this
Seventh Day of July, 2020

Andrei Iancu
*Director of the United States Patent and Trademark Office*